(12) United States Patent
Hatada et al.

(10) Patent No.: US 7,416,650 B2
(45) Date of Patent: Aug. 26, 2008

(54) GAS CONCENTRATION MEASURING APPARATUS

(75) Inventors: Yoshikazu Hatada, Chiryu (JP);
Noboru Yamamoto, Kariya (JP);
Hiroyuki Sakai, Okazaki (JP)

(73) Assignee: DENSO Corporation, Kariya (JP)

( * ) Notice: Subject to any disclaimer, the term of this patent is extended or adjusted under 35 U.S.C. 154(b) by 859 days.

(21) Appl. No.: 10/743,409

(22) Filed: Dec. 23, 2003

(65) Prior Publication Data

US 2004/0134782 A1 Jul. 15, 2004

(30) Foreign Application Priority Data

Dec. 26, 2002 (JP) ............................. 2002-377918
Oct. 29, 2003 (JP) ............................. 2003-369493

(51) Int. Cl.
*G01N 27/41* (2006.01)
(52) U.S. Cl. ...................... 204/406; 204/425; 73/23.31
(58) Field of Classification Search ................ 204/406, 204/424, 425, 426; 73/23.31
See application file for complete search history.

(56) References Cited

U.S. PATENT DOCUMENTS

| 4,030,190 | A | * | 6/1977 | Varker ........................... 29/852 |
| 4,112,893 | A | * | 9/1978 | Anzai ........................... 123/689 |
| 5,078,855 | A | * | 1/1992 | Mochizuki et al. ........... 204/418 |
| 5,150,189 | A | * | 9/1992 | Shirai et al. .................. 327/514 |
| 5,331,310 | A | * | 7/1994 | Stetter et al. ................. 340/632 |
| 5,672,811 | A | * | 9/1997 | Kato et al. .................... 73/31.05 |
| 6,547,955 | B1 | | 4/2003 | Hada et al. |
| 6,673,223 | B2 | * | 1/2004 | Kunimoto et al. ........... 204/426 |
| 6,849,174 | B2 | | 2/2005 | Hada et al. |

FOREIGN PATENT DOCUMENTS

| EP | 1 006 351 A1 * | 6/2000 |
| JP | 61-158162 | 7/1986 |
| JP | 62-202570 | 9/1987 |
| JP | 8-33965 | 3/1996 |
| JP | 2000-171435 | 6/2000 |

OTHER PUBLICATIONS

Skoog et al, Principles of Instrumental Analysis, 5th Edition, 1998, pp. 53-55.*
Japanese Office Action dated Nov. 14, 2006 with English translation.

* cited by examiner

*Primary Examiner*—Kaj K Olsen
(74) *Attorney, Agent, or Firm*—Nixon & Vanderhye P.C.

(57) ABSTRACT

In a gas concentration measuring apparatus, a measurement substrate is provided. A conductive pattern portion is formed in the measurement substrate. The conductive pattern portion includes a signal input pattern constituting the signal processing circuit and electrically connected to the connection terminal, said signal input pattern having direct current impedance with respect to the connection terminal, said direct current impedance being 10 percent or less of the input impedance of the connection terminal; a different potential pattern having a potential difference of 2 V or over from a potential of the signal input pattern; and a guard pattern having a substantially constant potential and a potential difference of less than 0.5 V from the potential of the signal input pattern, said guard pattern being arranged on at least a portion of the measurement substrate, said at least portion of the measurement substrate being located between the signal input pattern and the different potential pattern.

24 Claims, 12 Drawing Sheets

GAS CONCENTRATION MEASURING APPARATUS

BACKGROUND OF THE INVENTION

The present invention relates to a gas concentration measuring apparatus for measuring a concentration of a specified gas component contained in a gas.

Gas sensors are utilized for suitably controlling automobile engines in recent years. The gas sensors are configured to measure a concentration of a specified gas component, such as nitrogen oxides (NOx), carbon monoxide (CO), hydrocarbon (HC), oxygen ($O_2$), or the like, which is contained in exhaust emissions exhausted from the engines.

As one of the gas sensors, a gas sensor designed to output a sensor current according to the concentration of the specified gas component is generally used.

A gas concentration measuring apparatus including such a gas sensor is configured to measure the amount of the sensor current to measure the concentration of the specified gas component contained in a gas exhausted from an engine, an example of which has been disclosed in U.S. Patent Publication 6,547,955 (Japanese Patent Publication 2000-171435).

In this type of conventional gas concentration measuring apparatus including the gas sensor configured to output a sensor current in accordance with a concentration of a specified gas component, the sensor current outputted from the gas sensor is so weak as to be subject to electrical noises or the like.

For instance, the sensor current may be outputted as weak current of about a few nanoamperes (nA) from the gas sensor that measures the concentration of NOx as the specified gas component, requiring high measurement accuracy in 1 nanoampere (nA).

On the other hand, as materials of circuit substrates where electrical circuits are formed, an insulating material, such as glass epoxy resin, can be utilized. The circuit substrate made of an insulating material may cause weak leakage current to flow between copper patterns formed thereon that electrically connect electrical components with each other. Especially, under adverse environment of, for example, high temperature, high humidity or the like, the surface resistance of circuit substrate decreases, thereby excessively increasing the leakage current.

For example, when a circuit substance made of glass epoxy resin as the insulating material is used under high temperature and high humidity, the substrate resistance between the copper patterns adjacent to each other at intervals of about 0.5 mm may decrease up to about $10^{10}$ ohms ($\Omega$). In this case, there is the possibility that leakage current of about 1 nA (nanoampere) occurs due to a potential difference of about a few volts applied between the adjacent copper patterns.

As described above, in the conventional gas concentration measuring apparatus, the leakage current occurring in the circuit substrate used for measuring the sensor current outputted from the gas sensor causes the sensor current to fluctuate, and therefore, the leakage current contributes to block the sufficient improvement of measurement accuracy in the conventional gas concentration measuring apparatus.

SUMMARY OF THE INVENTION

The present invention is made on the background.

Accordingly, it is an object of the present invention to provide a gas concentration measuring apparatus with a gas sensor, which is capable of measuring a sensor current outputted from the gas sensor in high accuracy.

According to one aspect of the present invention, there is provided a gas concentration measuring apparatus comprising: a gas sensor configured to measure a concentration of a specified gas component contained in a gas and to output a sensor current corresponding to the measured concentration of the specified gas component; and a measurement substrate where an electric circuit is formed, said electric circuit being electrically connected to the gas sensor and including a signal processing circuit configured to measure the sensor current outputted from the gas sensor, wherein said electric circuit comprises: a connection terminal electrically connected to the gas sensor and configured to input the sensor current from the gas sensor, said connection terminal having input impedance of 500 k$\Omega$ or over; a conductive pattern portion having conductivity and formed in the measurement substrate; and an electric component mounted on the conductive pattern portion, said conductive pattern portion including: a signal input pattern constituting the signal processing circuit and electrically connected to the connection terminal, said signal input pattern having direct current impedance with respect to the connection terminal, said direct current impedance being 10 percent or less of the input impedance of the connection terminal; a different potential pattern having a potential difference of 2 V or over from a potential of the signal input pattern; and a guard pattern having a substantially constant potential and a potential difference of less than 0.5 V from the potential of the signal input pattern, said guard pattern being arranged on at least a portion of the measurement substrate, said at least portion of the measurement substrate being located between the signal input pattern and the different potential pattern.

According to another aspect of the present invention, there is provided a gas concentration measuring apparatus comprising: a gas sensor configured to measure a concentration of a specified gas component contained in a gas and to output a sensor current corresponding to the measured concentration of the specified gas component; and a measurement substrate where an electric circuit is formed, said electric circuit being electrically connected to the gas sensor and including a signal processing circuit configured to measure the sensor current outputted from the gas sensor, wherein said electric circuit comprises: a connection terminal electrically connected to the gas sensor and configured to input the sensor current from the gas sensor, said connection terminal having input impedance of 500 k$\Omega$ or over; a conductive pattern portion having conductivity and formed in the measurement substrate; and an electric component mounted on the conductive pattern portion, said conductive pattern portion including: a signal input pattern constituting the signal processing circuit and electrically connected to the connection terminal, said signal input pattern having direct current impedance with respect to the connection terminal, said direct current impedance being 10 percent or less of the input impedance of the connection terminal; a different potential pattern having a potential difference of 2 V or over from a potential of the signal input pattern; and a guard pattern having a substantially constant potential within a range from 80 percent or more to 120 percent or less of the potential of the signal input pattern, said guard pattern being arranged on at least a portion of the measurement substrate, said at least portion of the measurement substrate being located between the signal input pattern and the different potential pattern.

BRIEF DESCRIPTION OF THE DRAWINGS

Other objects and aspects of the invention will become apparent from the following description of an embodiment with reference to the accompanying drawings in which.

DETAILED DESCRIPTION OF EMBODIMENTS OF THE INVENTION

Embodiments of the invention will be described hereinafter with reference to the accompanying drawings.

First Embodiment

Figure 1:
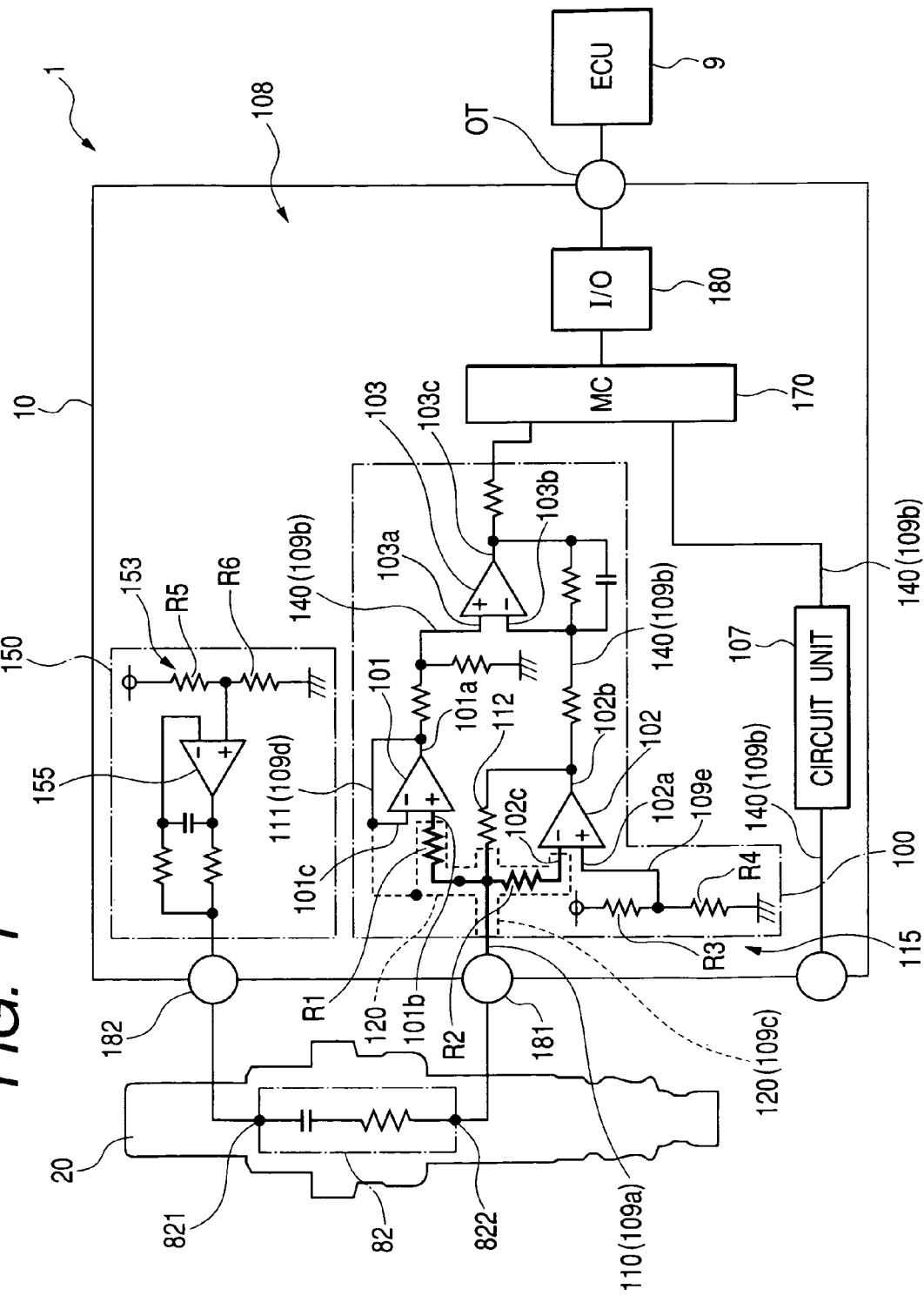
FIG. 1 is a circuit diagram of a gas concentration measuring apparatus according to a first embodiment of the invention.

FIG. 1 illustrates a block diagram showing an overall structure of a gas concentration measuring apparatus 1 according to a first embodiment of the invention.

The gas concentration measuring apparatus 1 comprises a gas sensor 20 having a gas sensor element 8 and configured to measure a concentration of a specified gas component, such as nitrogen oxides (NOx), carbon monoxide (CO), hydrocarbon (HC), oxygen ($O_2$), or the like, contained in a gas for measurement, and a measurement substrate 10 where a circuit unit 107 and an electric circuit 108 are formed.

The electric circuit 108 includes a signal processing circuit 100 for measuring a sensor current outputted from the gas sensor 20.

Figure 6:
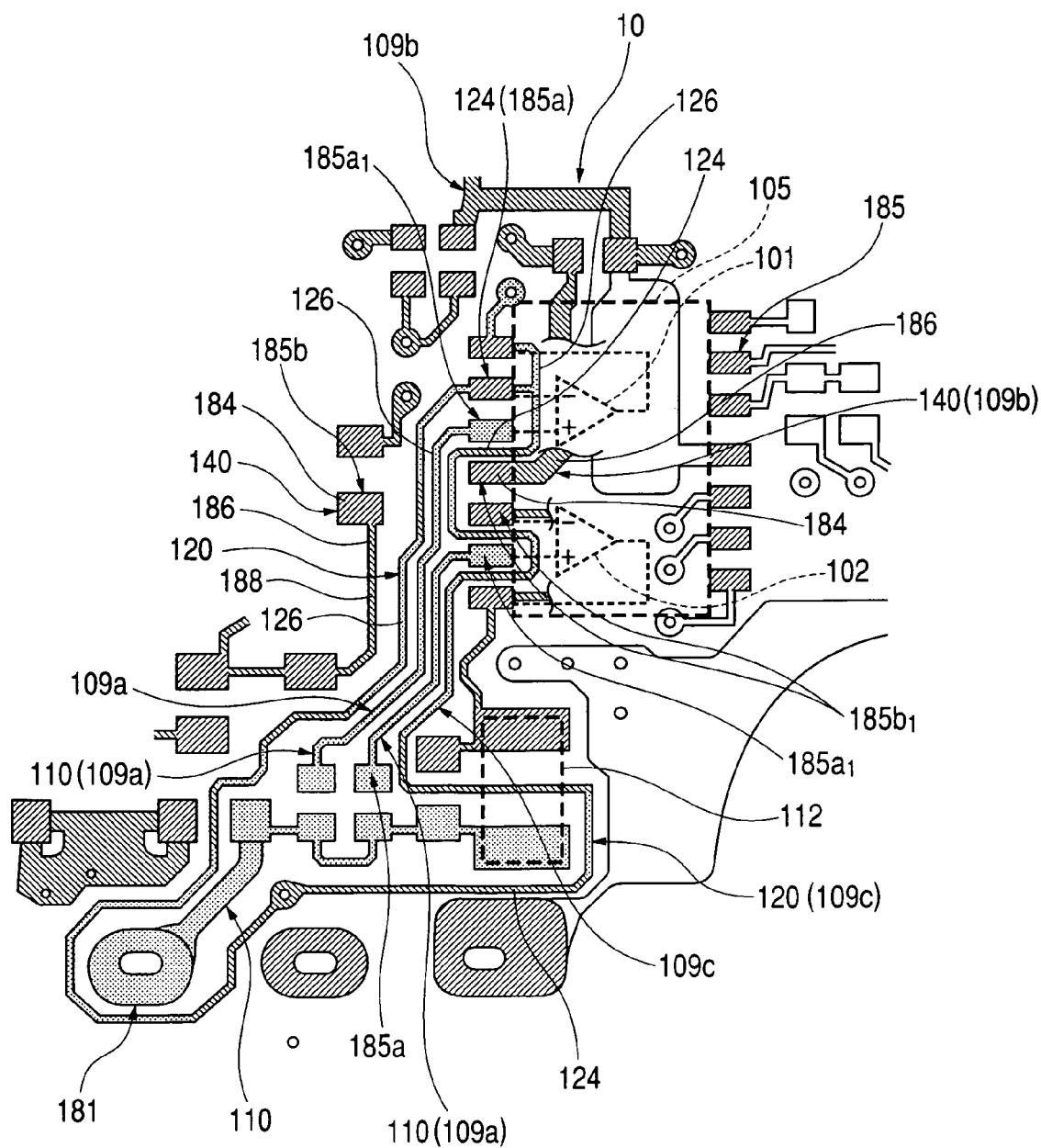
FIG. 6 is a view showing conductive patterns arranged on the measurement substrate shown in FIG. 5 according to the first embodiment.

The electric circuit 108, as shown in FIGS. 1 and 6, comprises an IC (integrating circuit) 105 surface-mounted on a surface of the measurement substrate 10, a connection terminal 181 having an input impedance of 500 kilo ohms (k$\Omega$) or more, a plurality of electric components, described hereinafter, that are mounted on the surface of the measurement substrate 10, and a conductive pattern portion 109 formed on the surface thereof for electrically connecting the electric components.

The conductive pattern portion includes conductive patterns 109a, 109b, 109c, 109d and 109e.

The conductive patterns 109a are signal input patterns 110 that are components of the signal processing circuit 100 and that are electrically connected to the connection terminal 181. Each of the input patterns 110 has a potential difference of approximately 2 k$\Omega$ and below with respect to the connection terminal 181.

The conductive patterns 109b are different potential patterns 140 each having a potential difference of not less than approximately 2 volts (V) with respect to the signal input patterns 110.

The conductive pattern 109c is a guard pattern 120 having a substantially constant potential throughout itself, and the constant potential of the conductive pattern 109c is substantially set within a range from 80 percent or more to 120 percent or less of the potential of each of the signal input patterns 110.

In this first embodiment, the potential difference between the conductive pattern 109c and each of the signal input patterns 110 is set to approximately less than 0.5 volts (V).

The conductive pattern 109d is a portion of a signal measurement pattern 111 constituting a path with output impedance of 500 $\Omega$ or less with respect to the ground of the measurement substrate 10.

The guard pattern 120 is arranged at a portion of the surface of the measuring substrate 10, portion which is located between the signal input patterns 110 and the different potential patterns 140.

The electrical circuit 108 also comprises, as the electric components, a power supply circuit 150 and a connection terminal 182 that are electrically connected with each other.

Figure 3:
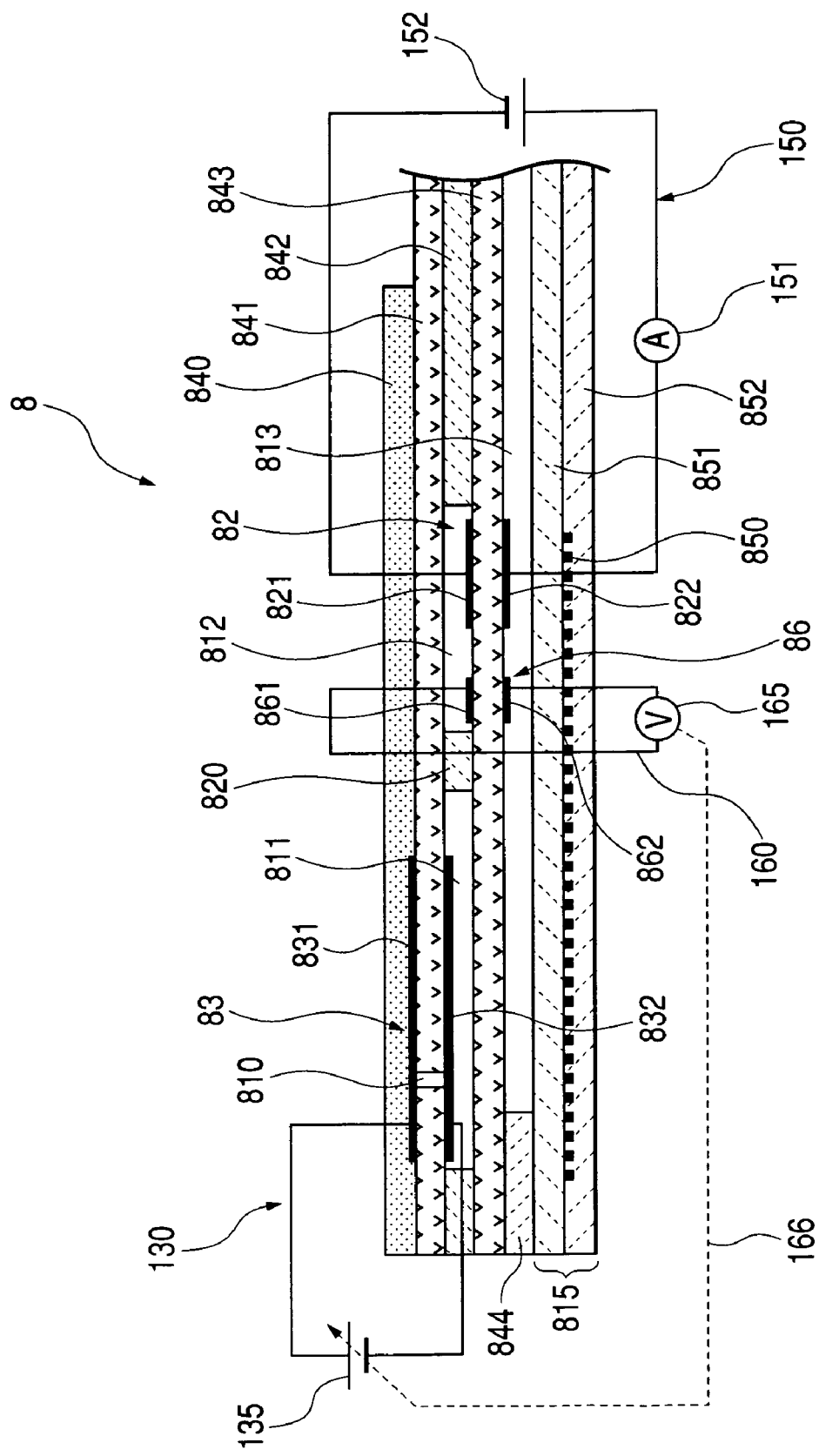
FIG. 3 is a cross sectional view showing an internal structure of a gas sensor element shown in FIG. 2 according to the first embodiment.

The circuit unit 107 includes a pump circuit 130 having a power supply 135, as shown in FIG. 3.

Figure 2:
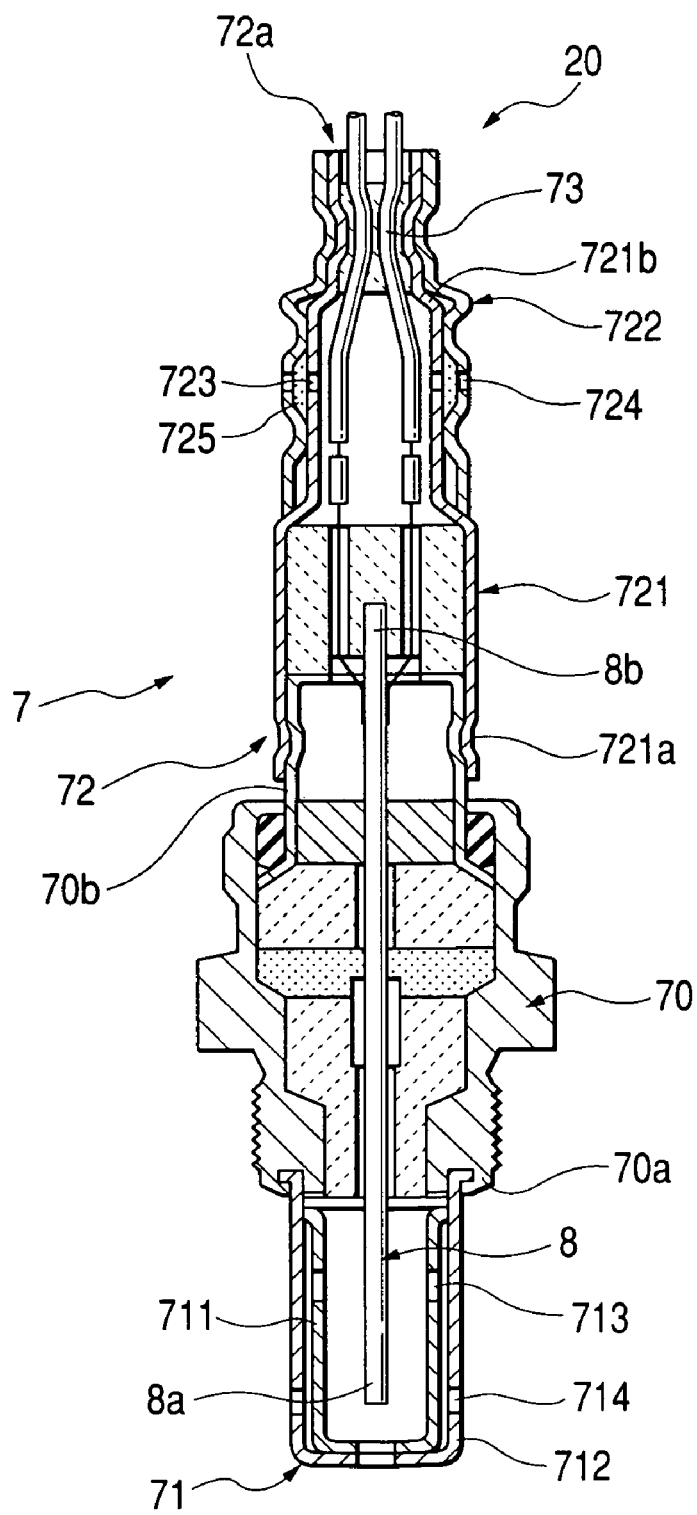
FIG. 2 is a longitudinal cross sectional view showing an overall structure of a gas sensor shown in FIG. 1 according to the first embodiment.

On the other hand, as shown in FIG. 2, the gas sensor 70 including the gas sensor element 8 is attached to an exhaust pipe (not shown) of an automobile engine and used for combustion control of the engine, monitor of catalyst for emission gas purification, or the like. The gas sensor 70 is configured to measure the concentration of the NOx, as an example of the specified gas component in this first embodiment, contained in the gas exhausted through the exhaust pipe.

The gas sensor 20 of the first embodiment, as shown in FIG. 2, comprises a cylindrical housing 70 and the gas sensor element 8 whose outer peripheral portion is supported by an insulating member. The gas sensor element 8 is contained in the cylindrical housing 70, and one end portion 8a of the gas sensor element 8 projecting outwardly through one end portion 70a of the housing 70 is contained in a cylindrical shaped exhaust cover 71 fixed to the one end portion thereof.

The exhaust cover 71 has a double structure of an inner cover 711 and an outer cover 712 so that the outer cover 712 surrounds an outer peripheral sidewall of the inner cover 711. The inner cover 711 and the outer cover 712 are made of, for example, stainless-steel, respectively.

The covers 711 and 712 are formed at their outer peripheral sidewalls and bottom walls with introduction holes 713, 714, respectively, so that they allow the exhaust gas to be introduced into an inner hollow portion of the exhaust cover 71.

The gas sensor 20 is also provided, as shown in FIG. 2. at other end portion 70b of the housing 70 with an air cover 72. The air cover 72 is fixed at the other end portion 70b of the housing 70. The air cover 72 comprises a cylindrical main cover 721 and a cylindrical sub cover 722. One end portion 721a of the main cover 721 is secured to the other end portion 70b of the housing 70 and the sub cover 722 surrounds other end portion 721b of the main cover 721.

The main cover 721 is provided with air introduction holes 723 formed at predetermined positions of its peripheral side wall, and the sub cover 722 is also provided with air introduction holes 724 formed at predetermined positions of its peripheral side wall. Each position of each air introduction hole 723 of the main cover 721 is opposite to each position of each introduction hole 724 of the sub cover 722. The air introduction holes 723 and 724 permit air, which is reference gas, to be introduced into an inner hollow portion of the air cover 72.

As shown in FIG. 2, the gas sensor 20 also comprises a water-shedding filter 725 for the waterproofing of the inner hollow portion of the air cover 72. The water-shedding filter 725 is filled between the main cover 721 and sub cover 722 to cover the introduction holes 723 and 724. The air cover 72 is formed at its other end portion with an opening portion 72a so that lead wires 73 connected to other end portion 8b of the gas sensor element 8 project through the opening portion 72a outside the air cover 72.

The gas sensor element 8, as shown in FIGS. 3. and 4, comprises first and second solid electrolyte members 841 and 843 each shaped like a seat and arranged in parallel. The gas sensor element 8 also comprises a spacer 842 interposed between the first and second solid electrolyte members 841 and 843.

The spacer 842 is formed with first and second holes 811a and 812a, and arranged between the first and second solid electrolyte members 841 and 843 so that the first and second solid electrolyte members 841 and 843, and the first and second holes 811a and 812a provide first and second chambers 811 and 812 thereamong.

The first and second chambers 811 and 812 allow the gas for measurement to be introduced therein.

The gas sensor element 8 also comprises a porous protection layer 840 having a seat shape and mounted on the first solid electrolyte member 841, a seat heater 815, a spacer 844 formed with a hole 813a and interposed between the seat heater 815 and the second solid electrolyte member 843 so that the heater 815, the hole 813a, and the second solid electrolyte member 843 provide a reference gas chamber 813 thereamong. The gas sensor element 8 has a laminated structure so that the heater 815, the spacer 844, the second solid electrolyte member 843, the spacer 842, the first solid electrolyte member 841 and the porous protection layer 840 are laminated in this order with each other.

Each of the spacers 842 and 844 is made of, for example, an insulating alumina, and the porous protection layer 840 is made of, for example, an insulating ceramic.

The gas sensor element 8 further comprises a sensor cell 82 that is provided with a portion of the second solid electrolyte member 843 and a pair of first and second sensor electrodes 821, 822 mounted on surfaces of the portion of the second electrolyte member 843, respectively.

The first sensor electrode 821 is opposite to the second chamber 812, and the second sensor electrode 822 faces the reference gas chamber 813 into which the air as the reference gas can be introduced.

The first sensor electrode 821 is electrically connected to the connection terminal 182. The connection terminal 182 is disposed to the measurement substrate 10 and extends from the power supply circuit 150 with a lead wire of a connection cable. The second sensor electrode 822 is electrically connected to the connection terminal 181 disposed to the measurement substrate 10. The connection terminal 181 extends from the signal processing circuit 100 with a lead wire of a connection cable.

That is, as shown in FIG. 1, the first sensor electrode 821 is electrically connected through the connection terminal 182 to the power supply circuit 150, and the second sensor electrode 822 is electrically connected through the connection terminal 181 to the signal processing circuit 100.

The sensor cell 82 is operative to output the sensor current corresponding to the concentration of the specified gas component contained in the gas for measurement according to a predetermined voltage applied between the first and second sensor electrodes 821 and 822.

The gas sensor element 8 further comprises a pump cell 83 that is provided with a portion of the first solid electrolyte member 841 and a pair of first and second pump electrodes 831, 832 mounted on surfaces of the portion of the first electrolyte member 841, respectively.

The first and second pump electrodes 831 and 832 are electrically connected to the pump circuit 130 (power supply 135).

The first pump electrode 831, as shown in FIG. 3, is opposite through the porous protection layer 840 to an exterior of the gas sensor element 8, and the second pump electrode 832 faces the first chamber 811.

One end portion of the first solid electrolyte member 841, which is located between the first and second pump electrodes 831 and 832, is formed with a first diffusion resistance passage 810, such as a pin hole or a fine pore, penetrating therethrough. The first chamber 811 is communicated through the first diffusion resistance passage 810 with the exterior of the gas sensor element 8.

A second diffusion resistance passage 820, such as a pin hole or a fine hole, is formed in the spacer 842 that is located between the first and second chambers 811 and 812 so that the first chamber 811 can be communicated with the second chamber 812 through the second diffusion resistance passage 820.

Incidentally, each of the first and second diffusion resistance passages 810 and 820 may be composed of, for example, porous layer The pump cell 83 is operative to pump oxygen ions corresponding to the applied voltage between the first and second pump electrodes 831 and 832.

The gas sensor element 8 further comprises a monitor cell 86 that is provided with another portion of the second solid electrolyte member 843 and a pair of first and second monitor electrodes 861, 862 mounted on surfaces of another portion of the second electrolyte member 843, respectively.

The first and second monitor electrodes 861 and 862 are electrically connected to a monitor circuit 160 having a voltmeter 165 that constitutes the electric circuit 108 on the measurement substrate 10.

The first monitor electrode 861, as shown in FIG. 3, is opposite to the second chamber 812, and the second monitor electrode 862 faces the reference gas chamber 813.

The circuit unit 107 also comprises a feedback circuit 166 electrically connected between the pump circuit 130 and the monitor circuit 160.

Figure 4:
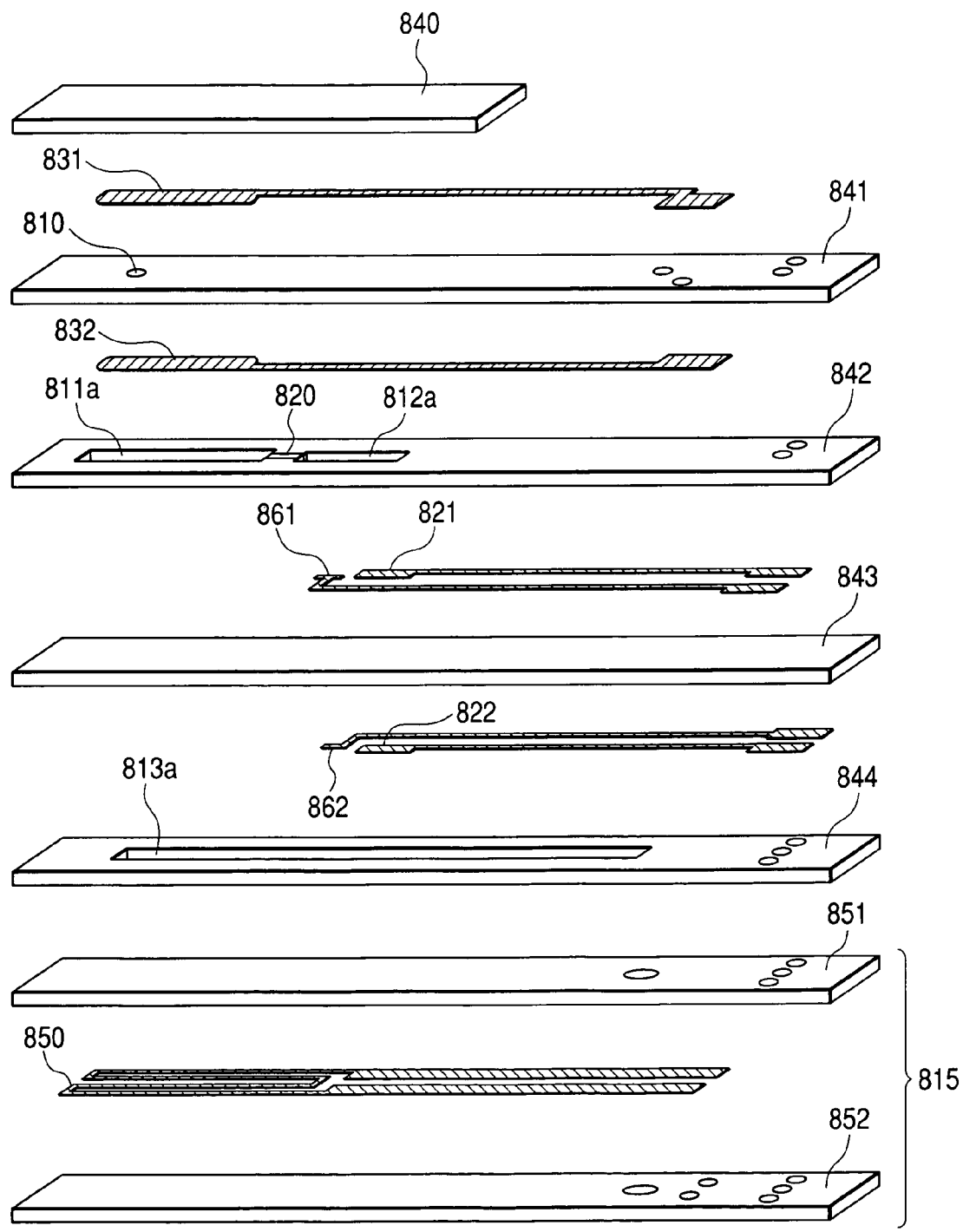
FIG. 4 is an exploded perspective view showing a laminated structure of the gas sensor element shown in FIG. 3 according to the first embodiment.

As shown in FIGS. 3 and 4, each of the first and second solid electrolyte members 841 and 843 is made of, for example, oxygen-ion conductive zirconia. Each of the first pump electrode 831, the second sensor electrode 822, and the second monitor electrode 862 is made of noble metal, such as platinum (Pt). Each of the second pump electrode 832 and the first monitor electrode 861 is made of noble metal, such as platinum (Pt)—gold (Au), which is inactive against nitrogen oxides (NOx). The first sensor electrode 821 is made of noble metal, such as rhodium (Rh), or Pt—Ph (phenyl), which is active against NOx.

In this specification, "material such as noble metal is active against NOx" means that the material has decomposition effects of NOx into oxygen ions and hydrogen ions, and "material such as noble metal is inactive against NOx" means that the material does not have the decomposition effects.

The heater 815, as shown in FIGS. 3 and 4, comprises insulating heater substrates 851 and 852, and a heating element 850 located between the insulating heater substrates 851 and 852 so that they are laminated with each other. The heating element 850 is subjected to electric power supplied from an exterior of the heater 815 so as to generate heat.

Each of the heater substrates 851 and 852 is made of, for example, alumina, and the heating element 850 is made of noble metal, such as platinum.

Next, the measurement substrate 10 for controlling the gas sensor element 8 of the gas sensor 70 will be explained hereinafter.

On the measurement substrate 10, the electric circuit 108 is mounted. The electric circuit 108 includes the electric circuit 150 electrically connected to the sensor cell 82, the signal processing circuit 100, a microcomputer 170 (shown as "MC" in FIG. 1) and an I/O (input/output) circuit 180 (shown as "I/O" in FIG. 1) electrically connected to the microcomputer 170 and an engine control unit (ECU) electrically connected through an output terminal OT to the I/O circuit 180. The ECU 9 is arranged at an exterior of the gas concentration measuring apparatus 1 and controls the engine (not shown) electronically.

In addition, on the measurement substrate 10, the pump circuit 130, the feedback circuit 166 and peripheral components (not shown) of the microcomputer 170 electrically connected thereto are mounted as the circuit unit 170, respectively.

The power supply circuit 150, as shown in FIG. 1, is a circuit configured to apply voltage on the sensor cell 82 (an equivalent circuit in FIG. 1) of the gas sensor 20. The signal processing circuit 100 is a circuit for converting the sensor current into a voltage signal.

Figure 5:
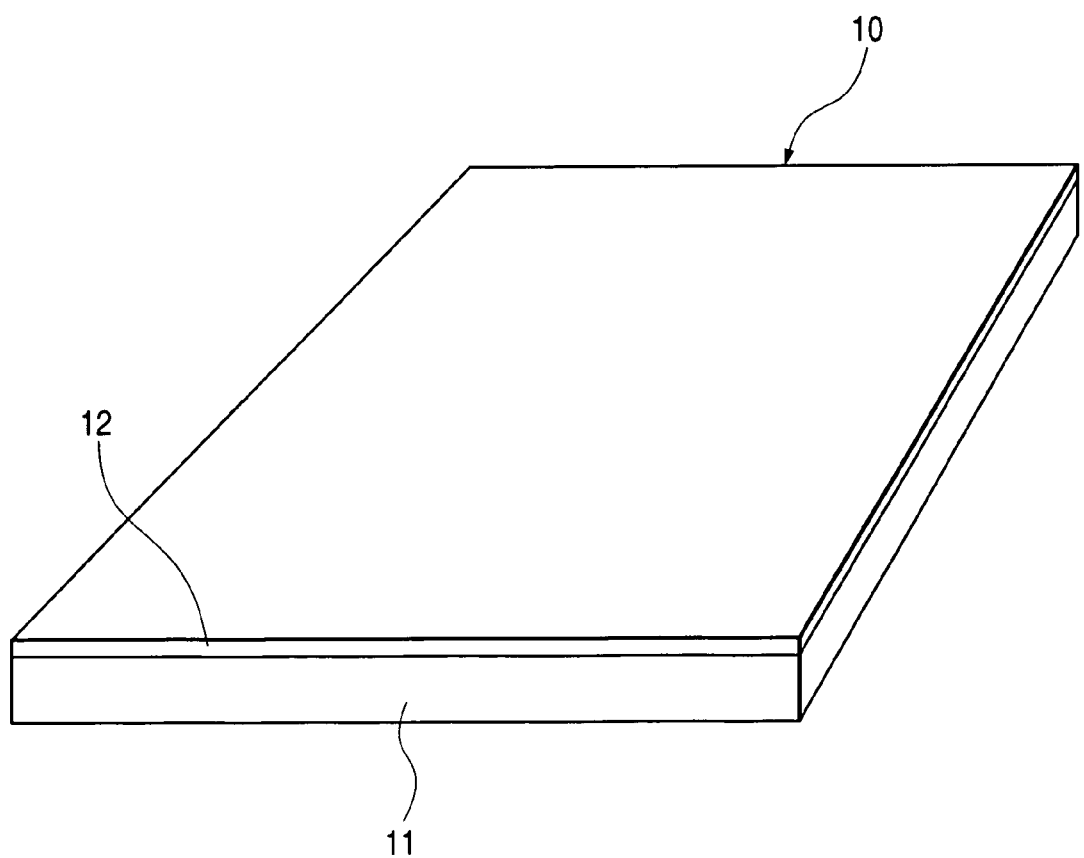
FIG. 5 is a perspective view illustrating a measurement substrate shown in FIG. 1 according to the first embodiment.

The measurement substrate 10 of this first embodiment, as shown in FIG. 5 that omits the conductive patterns and the electric components, is a glass-epoxy substrate with a single layer structure, which is composed of a single insulating layer 11 and a surface conductive layer 12 as a single conductive layer mounted on one surface of the single insulating layer 11.

The conductive pattern portion 109 (109a to 109c) is formed in the surface conductive layer 12, and the electric components are mounted therein so that the circuit unit 107 and the electric circuit 108 including the power supply circuit 150, the signal processing circuit 100 and so on are formed in the surface conductive layer 12.

The signal processing circuit 100, as shown in FIG. 1, comprises three operational amplifiers 101 to 103, a resistor 112 as shunt resistance and so on. The signal processing circuit 100 is configured to input the sensor current flowing into the measurement substrate 10 from the second sensor electrode 822 and to convert the inputted sensor current into the voltage signal.

The operational amplifier 101, as shown in FIG. 1, has an output terminal 101a, a non-reverse input terminal 101b, and a reverse input terminal 101c. The operational amplifier 101 has a gain of approximately 1 so as to be served as a voltage signal measuring buffer for outputting the potential that equals to that of the connection terminal 181 through the output terminal 101a.

The operational amplifier 102 is configured to control that the potential applied on its non-reverse input terminal 102a (+) substantially coincides with the potential of the connection terminal 181.

The operational amplifier 103 has a non-reverse input terminal 103a electrically connected to the output terminal 101a of the operational amplifier 103, a reverse input terminal 103b electrically connected to the output terminal 102b of the operational amplifier 102, and an output terminal 103c.

That is, the operational amplifier 103 is configured to amplify the voltage difference between the voltage of the output terminal 101a of the operational amplifier 101 and that of the output terminal 102b of the operational amplifier 102, thereby outputting the voltage difference to the microcomputer 107 through the output terminal 103c.

The non-reverse input terminal 101b (+) of the operational amplifier 101 is electrically connected through a resistor R1 with direct impedance of 2 kΩ or less to the connection terminal 181.

The output terminal 102b of the operational amplifier 102, as shown in FIG. 1, is electrically connected to the reverse terminal 102c (−) thereof through the resistor 112 with high resistance of approximately 1.5 MΩ.

The reverse input terminal 102b of the operational amplifier 102 is electrically connected through a resistor R2 with direct impedance of 2 kΩ or less to the connection terminal 181.

The non-reverse input terminal 102a of the operational amplifier 102 is electrically connected through the conductive pattern 109e to a voltage dividing circuit 115 having a pair of resistors R1 and R2 so that the voltage dividing circuit 115 divides a supply voltage of the measurement substrate 10 by the pair of resistors R3 and the R4 to obtain a reference voltage of 4.4 V, whereby, on the non-reverse input terminal 102a, the reference voltage of 4.4 V is applied.

The power supply circuit 150, as shown in FIG. 1, comprises a voltage dividing circuit 153 including a pair of resistors R5 and R6 that divides a supply voltage of the measurement substrate 10 by the pair of resistors R5 and the R6, and an operational amplifier 155 that amplifies the voltage divided by the voltage dividing circuit 153 to apply the amplified voltage on the sensor cell 82 through the connection terminal 182. In this first embodiment, the voltage of 4.4 volts (V) is applied on the first sensor electrode 821 of the sensor cell 82 through the connection terminal 182.

The resistor 112 generates the potential difference between its both ends relative to the sensor current of the sensor cell 82. The operational amplifier 102 is configured to control that the potential applied on its non-reverse input terminal 102a substantially coincides with the potential of the connection terminal 181.

That is, the potential of the connection terminal 181 drops across the resistor 112 so that the voltage generated by reducing the voltage drop across the resistor 112 from the potential of the connection terminal 181 is outputted to the output terminal 102b of the operational amplifier 102.

Incidentally, in the measurement substrate 10 of this first embodiment, the potential of the connection terminal 181 electrically connected to the second sensor electrode 822 is controlled to become 4.0 (V). In addition, the voltage of 4.4 (V) is applied on the connection terminal 182 electrically connected to the first sensor electrode 821.

As described above, in the gas sensor 20 of this first embodiment, the potential difference of 0.4 (V) is applied across the sensor cell 82.

The microcomputer 170, as shown in FIG. 1, is configured to convert the analog voltage outputted from the output terminal 103c of the operational amplifier 103 into digital data, and to divide the digital voltage data by the resistance value of the resistor 112, thereby obtaining the value of the sensor current.

The microcomputer 170 is also configured to output a gas concentration signal through the I/O circuit 180 and the output terminal OT to the ECU 9 for electronically controlling the engine.

As shown in FIG. 1, in the signal processing circuit 100 on the measurement substrate 10, the input impedance of the connection terminal 181 is set to be not less than 500 kΩ.

On the other hand, the direct current impedance between the connection terminal 181 and each of the conductive patterns 109a constituting the paths from the connection terminal 181 to the operational amplifier 101 through the resistor R1, the resistor 112, and the operational amplifier 102 through the resistor R2 is set to be low, such as 2 kΩ or less.

The conductive patterns 109a constituting the paths from the connection terminal 181 to the non reverse input terminal 101b of the operational amplifier 101, the resistor 112, and the reverse input terminal 102c of the operational amplifier 102 provide a high impedance portion in accordance with the input impedance of the connection terminal 181.

In contrast, each of the operational amplifiers 101 and 102 has ideally infinite direct current impedance so that the direct current impedance between the connection terminal 181 and each of the conductive patterns 109b electrically connected to the output terminals 101a and 102b of the operational amplifiers 101 and 102 is high.

The resistance value of resistor 112 is set to 1.5 MΩ so that the direct current impedance between the connection terminal 181 and each of the conductive patterns 109b electrically connected to the microcomputer side of the resistor 112 is set to be substantially 1.5 MΩ.

Figure 7:
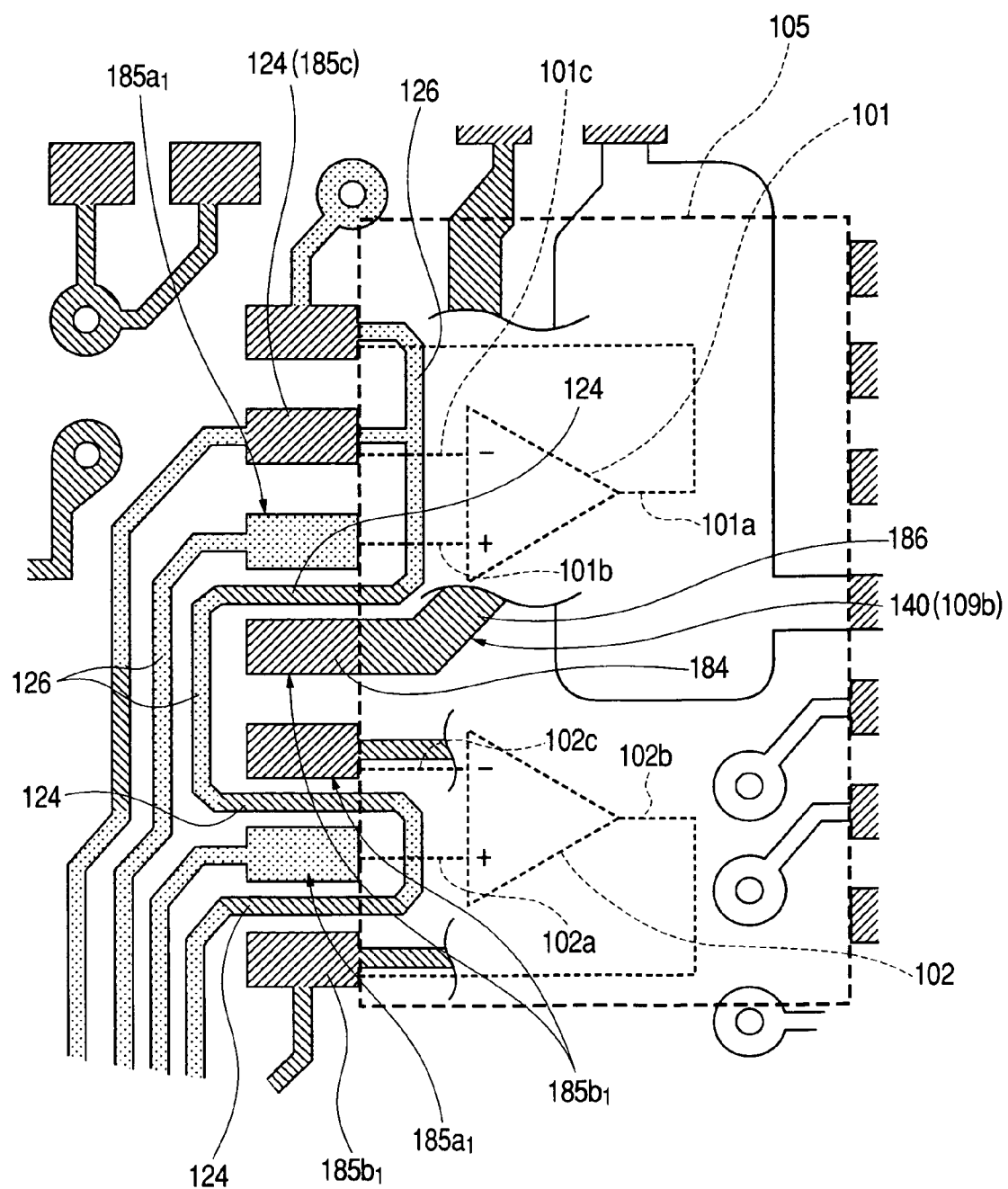
FIG. 7 is an enlarged view of a periphery of an IC shown in FIG. 6 according to the first embodiment.

In the signal processing circuit 100 mounted on the measurement substrate 10, therefore, as shown in FIGS. 1, 6 and 7, the conductive patterns 109a constituting paths from the connection terminal 181 to the non-reverse input terminal 101b of the operational amplifier 101, the resistor 112, and the reverse input terminal 102c of the operational amplifier 102 are set as the signal input patterns 110.

In addition, as shown in FIGS. 1, 6 and 7, the conductive patterns 109b electrically connected to the output terminals output terminals 101a, 102b of the operational amplifiers 101, 102 and the microcomputer side of the resistor 112 are set as the different conductive patterns 140 each having a differential potential from the signal input patterns 110.

Furthermore, as shown in FIGS. 1, 6 and 7, the guard pattern 120 as the conductive pattern 109c is arranged to surround the signal input patterns 110, and the guard pattern 120 is also electrically connected to the conductive pattern 109d electrically connected to the output terminal 101a of the operational amplifier 101, which is controlled to be substantially equivalent with respect to the connection terminal 181.

In this first embodiment, in the guard pattern 120, no electrical elements are incorporated so that the guard pattern 120 is made of only metallic foil on the measurement substrate 10.

Incidentally, electrical elements, such as resistors or jumper wires, may be incorporated in the guard pattern 120. In this case, it is necessary to limit the potential of the guard pattern 120 within approximately plus or minus 1 V.

Because the potential of the guard pattern 120 is limited within approximately plus or minus 1 V, it can be considered that the guard pattern 120 substantially keeps the constant potential throughout itself.

That is, in this first embodiment, when the electric circuit 108 operates, in order to suppress an adverse effect of the different potential patterns 140 with respect to the signal input patterns 110, the guard pattern 120 are so extended more than necessary as to be arranged the guard pattern 120 between the signal input patterns 110 and the different potential patterns 140.

The guard pattern 120, therefore, prevents the leakage current from flowing into the signal input patterns 110 from the different potential patterns 140, and from outflowing from the signal input patterns 110 into the different potential patterns 140.

In addition, the conductive pattern 109d that is electrically connected between the output terminal 101a of the operational amplifier 101 and the reverse input terminal 101c thereof constitutes the signal processing circuit 100 and the signal measurement pattern 111 constituting the path having output impedance of 500 Ω and below with respect to the ground of the measurement substrate 10.

The signal measurement pattern 111 is electrically connected to the guard pattern 120.

Incidentally, FIG. 6 shows the periphery of the signal processing circuit 100 in the electric circuit 108 mounted on the measurement substrate 10. FIG. 6 also shows the arrangement of the conductive patterns 109a to 109c on the measurement substrate 10 before the electric components are mounted thereon. FIG. 7 shows the enlarged view of the periphery of the IC 105 of FIG. 6.

In this first embodiment, the IC 105 that includes an internal circuit having the operational amplifiers 101 to 103, and the resistor 112 as the shunt resistance are surface-mounted on the measurement substrate 10.

Each of the different potential patterns 140, as shown in FIG. 6, includes exposed portions 184 around which no insulating coating is formed, and coating portions 186 that are formed by coating insulating coatings 188, such as green films, around the exposed portions 184. The exposed portions are portions, such as land portions 185b, that can be electrically connected the electric components, lead wires and so on.

The guard pattern 120, as shown in FIGS. 6 and 7, includes exposed adjacent portions 124, that are shown as "dot hatched area", arranged adjacent to the exposed portions 184, and coating adjacent portions 126, that are shown as "cross hatched area", arranged adjacent to the coating portions 186.

That is, the state of coating of the guard pattern 120 and that of coating of the different potential patterns 140 substantially coincide with each other on the measurement substrate 10 in this first embodiment, allowing the leakage current to be apt to occur between the exposed adjacent portion 124 of the guard pattern 120 and each of the exposed portions 184 of the different potential patterns 140.

In contrast, it is possible to prevent the leakage current from occurring between the coating adjacent portion 126 of the guard pattern 120 and each of the coating portions 186 of the different potential patterns 140.

In particular, the land portions 185a of the signal input pattern 110 include land portions 185a1, and the land portions 185b of the different potential patterns 140 include the land portions 185b1.

As shown in FIGS. 6 and 7, the land portions 185a1 and 185b1 are arranged on the measurement substrate 10 so as to correspond to the terminals of the IC 105, respectively, so that the land portions 185a1 and 185b1 are electrically connected to the terminals of the IC 105, respectively.

Each of the distances between the adjacent land portions 185a1, 185b1 is approximately 0.6 mm in accordance with each distance of, for example, 1.27 mm of each terminal of the IC 105.

In this first embodiment, therefore, on the measurement substrate 10, the guard pattern 120 is arranged on the distances between the land portions 185a1 of the signal input patterns 110 and the land portions 185b1 of the different potential patterns 140.

That is, the land portions 185b1 of the different potential patterns 140 are the exposed portions 184 each having no insulating film 188 so that, as shown in FIGS. 6 and 7, the exposed adjacent portions 124 of the guard pattern 120 are arranged in adjacent to the exposed portions 184 and between the land portions 185b1 and the land portions 185a1.

In addition, the electrodes of the IC 105 corresponding to the reverse input terminal 101c of the operational amplifier 101 is electrically connected to a land portion 185c of the guard pattern 120.

Next, the measurement operation of the gas concentration measuring apparatus 1 comprising the gas sensor 20 and the measurement substrate 10 will be described hereinafter.

At first, the operation of measuring the NOx gas will be explained.

The exhaust gas exhausted through the exhaust pipe of the engine (not shown), as shown in FIG. 3, is introduced through the porous protection layer 840 and the first diffusion resistance passage 810 into the first chamber 811. The introduced amount of the exhaust gas is determined by the diffusion resistance of the porous protection layer 840 and that of the first diffusion resistance passage 810.

Oxygen contained in the exhaust gas introduced in the first chamber 811, as shown in FIG. 3, becomes oxygen ions in the operation of the pump cell 82 so that the movement of the oxygen ions between the first chamber 811 and the exterior of the gas sensor element 8 through the pump cell 82 occurs. That is, the pumping of oxygen ions occurs in the first chamber 811.

As shown in FIG. 3, the electromotive force generated from the monitor cell 86 in the second chamber 812, which is served as oxygen concentration cell, is measured by the voltmeter 165 of the monitor circuit 160 mounted on the measurement substrate 10.

The feedback circuit 166 on the measurement substrate 10 feeds back the electromotive force detected by the monitor circuit 160 to the pump circuit 130 to execute feedback control of the pump cell 83.

That is, the feedback circuit 166 accordingly adjusts the voltage applied on the pump cell 83 according to the electromagnetic force generated in the monitor cell 86, thereby controlling the oxygen pumping amount by the pump cell 83.

In this first embodiment, as shown in FIG. 3, the feedback circuit 166 accordingly adjusts the voltage applied on the pump cell 83 according to the electromagnetic force generated in the monitor cell 86 so that the concentration of oxygen in the second chamber 812 is not more than 1 ppm. The gas sensor element 8 that keeps the concentration of oxygen in the second chamber 812 equal to or less than 1 ppm can measure the concentration of NOx in the exhaust gas introduced in the second chamber 812 with a high degree of accuracy.

As shown in FIG. 3, the sensor cell 82 having the first sensor electrode 821 opposite to the second chamber 812 and the second sensor electrode 822 facing the reference gas chamber 813 is subjected to the predetermined voltage between the first sensor electrode 821 and the second sensor electrode 822 so that the sensor cell 82 reduces the exhaust gas to resolve the NOx contained therein. In this first embodiment, when the NOx is reduced, the sensor cell 82 whose first and second sensor electrodes 821 and 822 between which the potential difference of 0.4 V is applied causes the sensor current with the amount corresponding to the concentration of the NOx contained in the exhaust gas to flow.

The sensor current, as shown in FIG. 1, is inputted from the connection terminal 181 into the signal processing circuit 100. The signal processing circuit 100 coverts the voltage drop across the resistor 112 into the voltage signal, voltage drop which is generated by causing the sensor current to flow through the resistor 112,. The signal processing circuit 100 outputs the voltage signal to the microcomputer 170.

The microcomputer 170 computes the sensor current value that the gas sensor 20 makes occur on the basis of the voltage signal and the resistance of the resistor 112, and converts the sensor current value into the concentration of NOx, thereby outputting the converted concentration of NOx to the ECU 9 through the output terminal OT.

According to this first embodiment, as described above, the guard pattern 120 that keeps substantially equipotential with respect to the connection terminal is arranged on the periphery of the signal input patterns 110 each having the potential difference of 2 kΩ or less with respect to the connection terminal 181 so that the guard pattern 120 prevents the leakage current from flowing into the signal input pattern 110 and from outflowing therefrom, signal input pattern 120 through which the sensor current that is weak current of approximately a few nA flows.

That is, when measuring the NOx as the specified gas component, the sensor current obtained by the gas sensor 20 is weak so that, when the leakage current may flow into the sensor current and/or outflow therefrom, it may be difficult to accurately measure the sensor current.

In addition, the surface resistance of the measurement substrate 10 between each of the different potential patterns 140 and each of the signal input patterns 110 decreases in proportion to the distance therebetween so that, when each distance between each of the different potential patterns 140 and each of the signal input patterns 110 is narrow, the large leakage current may flow therebetween based on Ohm's law.

However, in this first embodiment, the guard pattern 120 prevents the leakage current from flowing into each of the signal input patterns 110 and from outflowing therefrom, so that the measurement substrate 10 allows the amount of the sensor current that flows from the connection terminal 181 into the signal input patterns 110 to remain nearly unaffected by the different potential patterns 140.

The gas concentration measuring apparatus 1 including the measurement substrate 10 with the guard pattern 120 surrounding the signal input patterns 110 can measure the sensor current with a high degree of accuracy, and makes it possible to accurately measure the concentration of the NOx contained in the exhaust gas.

In particular, the measurement substrate 10 of this first embodiment is formed with the guard pattern 120 arranged on the distances between the land portions 185a1 and 185b1 of the IC 105.

That is, each of the distances between the adjacent land portions 185a1, 185b1 of the IC 105 is narrow of, for example, approximately 0.6 mm because the IC 105 has each narrow terminal distance of 1.27 mm, causing the leakage current to be apt to flow.

The measurement substrate 10, however, is formed with the guard pattern 120 arranged on the distances between the land portions 185a1 and 185b1 of the IC 105 so that it is possible to effectively prevent the leakage current from affecting the sensor current.

In addition, in this first embodiment, the signal measurement pattern 111 constitutes the path having output impedance of 500 Ω and below with respect to the ground of the measurement substrate 10 and the signal measurement pattern 111 is electrically connected to the guard pattern 120.

That is, because the signal measurement pattern 111 constitutes the path having output impedance of 500 Ω and below with respect to the ground of the measurement substrate 10, the potential of the signal measurement pattern 111 has a closely correlation with the potentials of the signal input patterns 110.

Therefore, the guard pattern 120 is electrically connected to the signal measurement pattern 111 so that it is possible to cause the potential of the guard pattern 120a to fluctuate with the fluctuations of the potentials of the signal input patterns 110, thereby preventing the fluctuations of the potential difference between the guard pattern 120a and each potential of each signal input pattern 110.

As a result, assuming that external conditions cause the potentials of the signal input patterns 110 to fluctuate, it is possible to prevent the potential difference between the guard pattern 120 and each of the signal input patterns 110 from fluctuating.

Furthermore, because the signal measurement pattern 111 electrically connected to the output terminal 101a of the operational amplifier 101 for outputting the potential that equals to that of the connection terminal 181 through the output terminal 101a is electrically connected to the guard pattern 120, it is possible to more prevent the potential difference between the guard pattern 120 and each of the signal input patterns 110.

Moreover, in this first embodiment, the potential of the guard pattern 120 may be substantially equivalent to that of the signal measurement pattern 111.

As a modification of this first embodiment, guard patterns may be accordingly mounted on necessary distances selected in all distances between the adjacent land portions 185a1, 185b1 of the IC 105 in place of the guard pattern 120 surrounding the signal processing patterns 110.

In this modification, each of the guard patterns needs to have a potential difference of 0.5 V or less with respect to the signal input patterns 110.

According to the modification, it is possible to prevent the leakage current in proportion to the ratio of the necessary distances to all distances between the adjacent land portions 185a1, 185b1 of the IC 105.

In this modification, respective adjacent guard patterns may be electrically connected with electrical elements such as jumper wires, resistors or the like on the ground that the structural circumstances of the arrangement of conductive patterns on the measurement substrate.

In this modification, it is necessary to limit the potentials of the respective adjacent guard patterns within approximately plus or minus 1 V, respectively.

Because the potentials of the respective adjacent guard patterns are limited within approximately plus or minus 1 V, respectively, it can be considered that the guard patterns substantially keep the constant potential throughout themselves, making it possible to make interchangeable the guard patterns with respect to the single guard pattern 120.

As another modification of this first embodiment, the guard patterns may be arranged on only some distances each having not more than 0.7 mm between the adjacent land portions 185a1, 185b1 of the IC 105. This structure can effectively prevent the leakage current in some distances each having 0.7 mm or less, in which the leakage current is apt to occur as compared with rest distances each having no less than 0.7 mm.

As further modification of this first embodiment, the guard patterns may be arranged on only some distances between some pairs of the adjacent land portions 185a1, 185b1 of the IC 105, wherein some signal input patterns 110 and some different potential patterns 140 corresponding to some pairs of the adjacent land portions 185a1, 185b1 of the IC 105 have potential differences of 2V or more, respectively.

This structure can effectively prevent the leakage current in some distances in which the leakage current is apt to occur as compared with rest distances corresponding to rest signal input patterns 110 and rest different potential patterns 140 have potential differences of less than 2V, respectively.

In a gas concentration measuring apparatus 1A of the further modification of this first embodiment, the guard pattern 120a can be electrically connected to the conductive pattern 109e that electrically connected between the non-reverse input terminal 102a of the operational amplifier 102 and the voltage dividing circuit 115.

Because the operational amplifier 102 is operative to control that the potential of the non-reverse input terminal 102a substantially equals to that of the connection terminal 181, the electrical connection of the guard pattern 120a to the non-reverse input terminal 102a of the operational amplifier 102 allows the potential of the guard pattern 120a to equal to each potential of each of the signal input patterns 110.

In this modification, the voltage applied on the non-reverse input terminal 102a of the operational amplifier 102 is obtained by dividing the supply voltage of the measurement substrate 10 by the pair of resistors R3 and R4 of the voltage dividing circuit 115.

Figure 8:
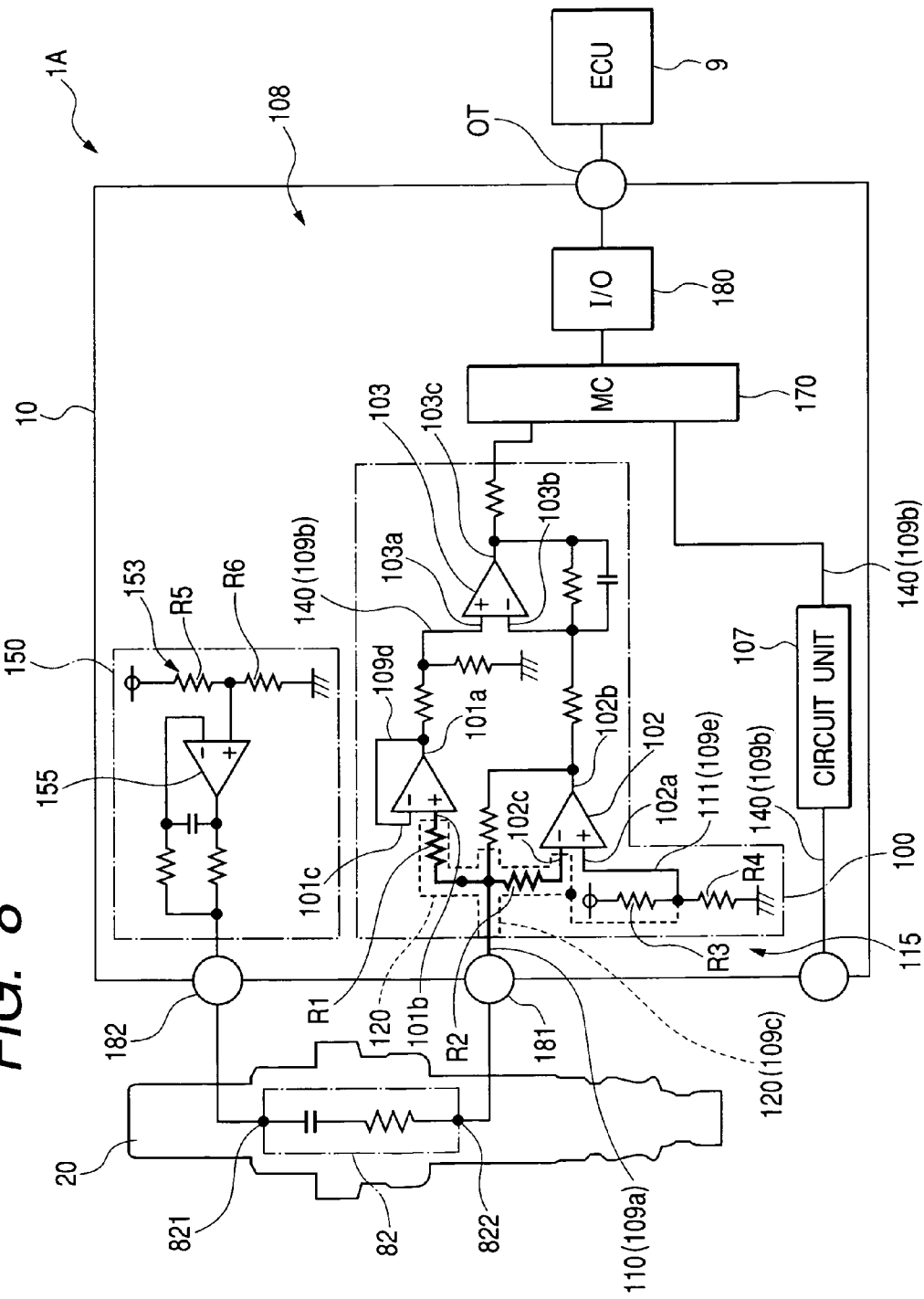
FIG. 8 is a circuit diagram of a gas concentration measuring apparatus according to a modification of the first embodiment.

The conductive pattern 109e, therefore, that electrically connected to the non-reverse input terminal 102a of the operational amplifier 102 constitutes the signal processing circuit 100 and a portion of the signal measurement pattern 111 constituting a path having output impedance of not more than 500 Ω with respect to the ground of the measurement substrate 10, shown in FIG. 8.

That is, because the supply voltage of the measurement substrate 10 has a different potential with respect to the signal input patterns 110, different potential which fluctuates with the potential of the potentials of the signal input patterns 110, the potential of the signal measurement pattern 111 has a closely correlation with the potentials of the signal input patterns 110.

Therefore, the guard pattern 120a is electrically connected to the signal measurement pattern 111 so that it is possible to cause the potential of the guard pattern 120a to fluctuate with the fluctuations of the potentials of the signal input patterns 110, thereby preventing the fluctuations of the potential difference between the guard pattern 120a and each potential of each signal input pattern 110.

As a result, assuming that external conditions cause the potentials of the signal input patterns 110 to fluctuate, it is possible to prevent the potential difference between the guard pattern 120a and each of the signal input patterns 110 from fluctuating.

Moreover, in this modification, the potential of the guard pattern 120a may be substantially equivalent to that of the signal measurement pattern 111.

Figure 9:
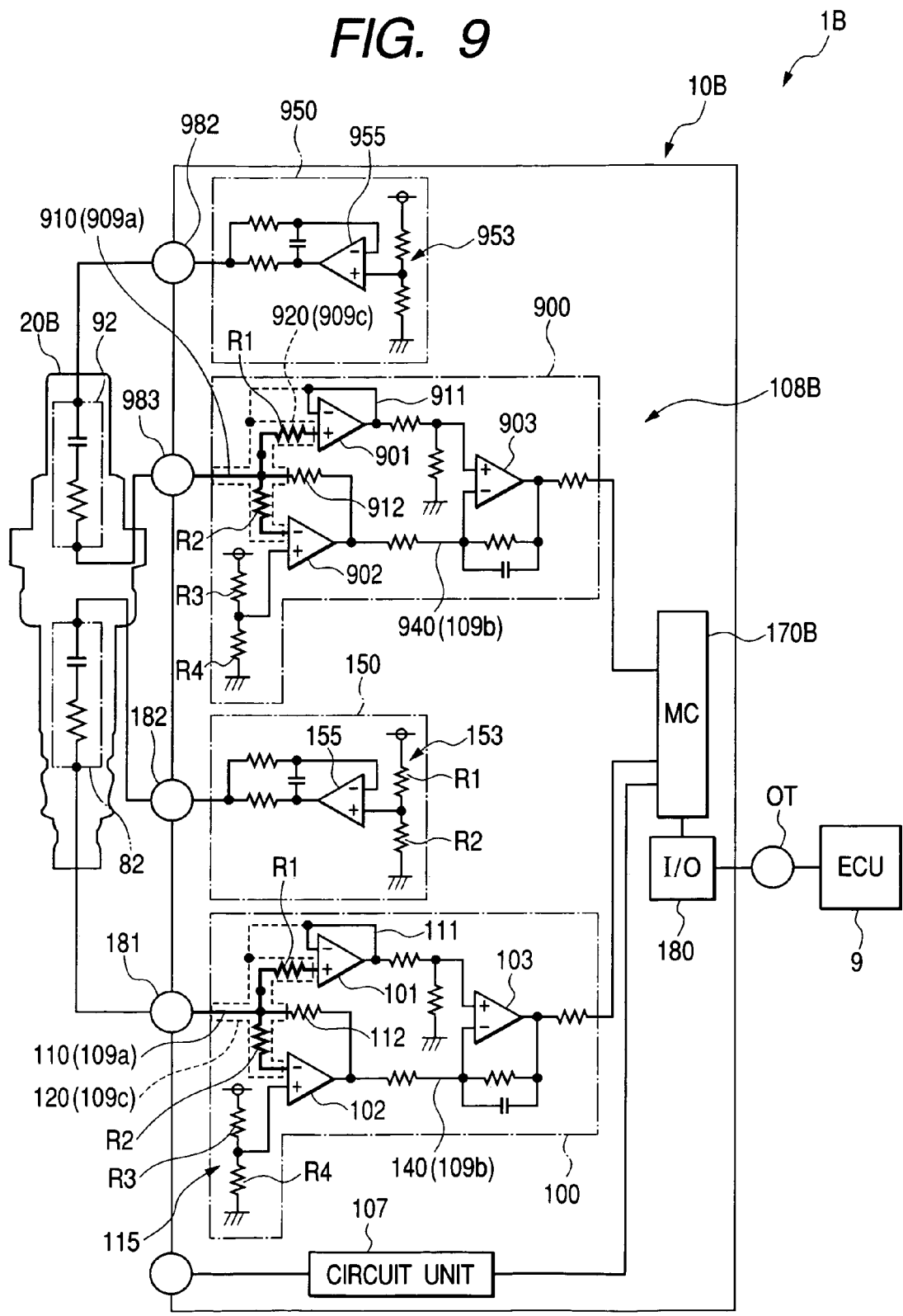
FIG. 9 is a circuit diagram of a gas concentration measuring apparatus according to another modification of the first embodiment.

In addition, as shown in FIG. 9, a gas concentration measuring apparatus 1B of further modification of this first embodiment comprises a gas sensor 20B further comprises a correction cell 92 having the same specification and structure of the sensor cell 82.

Furthermore, the gas concentration measuring apparatus 1B comprises an electric circuit 108B having a signal processing circuit 900 and a power supply circuit 150 mounted on the surface of the measurement substrate 10 in addition to the signal processing circuit 100 and the power supply circuit 150. The signal processing circuit 900 has the same specification and structure of the signal processing circuit 100, and the power supply circuit 950 has the same specification and structure of the power supply circuit 150.

That is, the signal processing circuit 900 comprises operational amplifiers 901 to 903, which correspond to operational amplifiers 101 to 103, a resistor 912 corresponding to the resistor 112, signal input patterns 910 (909a) corresponding to the signal input pattern 110, different potential patterns 940 (909b) corresponding to the different potential patterns 140 (109b), a guard pattern 920 (909c) corresponding to the guard pattern 120 (109c), and a signal measurement pattern 911 corresponding to the signal measurement pattern 111.

That is, in this modification, the guard pattern 920 corresponding to the guard pattern 120 is arranged on the measurement substrate 10B so as to surround the signal input patterns 910 corresponding to the signal input patterns 110.

Similarly, the power supply circuit 950 comprises a voltage dividing circuit 953 corresponding to the voltage dividing circuit, and an operational amplifier 955 corresponding to the operational amplifier 155.

The signal input patterns 910 (910a) is electrically connected to a connection terminal 981 corresponding to the connection terminal 181, and the power supply circuit 950 is electrically connected to a connection terminal 982 corresponding to the connection terminal 982.

The correction cell 92 is configured to measure the concentration of oxygen that remains in the second chamber 182 thereof.

That is, in this modification, the microcomputer 170B computes the sensor current value that the sensor cell 82 makes occur on the basis of the voltage signal obtained by the signal processing circuit 100 and the resistance of the resistor 112, and corrects the computed sensor current value of the sensor cell 82 on the basis of the sensor current value obtained by the sensor cell 92.

The modification allows, therefore, the accuracy of measuring the sensor current to be improved because the measured sensor current has substantially no influence of the remained oxygen concentration.

Incidentally, as the correction processing, the microcomputer 170B may compute an average of the computed sensor current value corresponding to the sensor cell 82 and the sensor current value obtained by the sensor cell 92.

Second Embodiment

Figure 10:
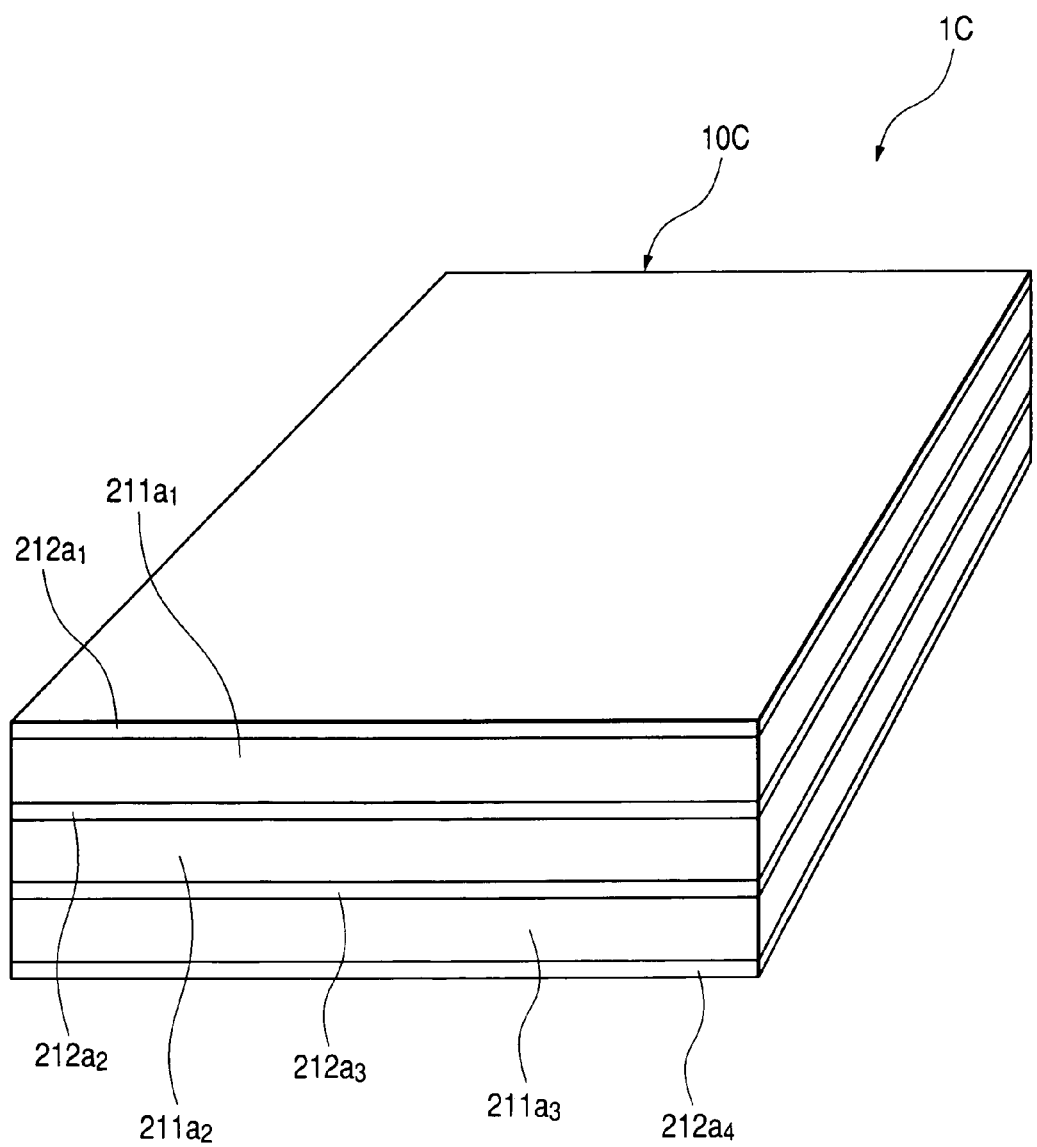
FIG. 10 is a perspective view illustrating a measurement substrate of a gas concentration measuring apparatus according to a second embodiment of the invention.

FIG. 10 illustrates a measurement substrate 10C of a gas concentration measuring apparatus IC according to the second embodiment.

In this embodiment, the measurement substrate 10 of the gas concentration measuring apparatus 1 is replaced with the measurement substrate 10C having a multilayered structure.

That is, the measurement substrate 10C of this second embodiment, as shown in FIG. 10 that omits the conductive patterns and the electric components, comprises a plurality of, for example, three insulating layers 211a1 to 211a3, and a plurality of, for example, four conductive layers 212a1 to 212a4 each having a surface on which the conductive patterns 109a to 109c are mounted. The conductive layers 212a1 to 212a4 and the insulating layers 211a1 to 211a3 are alternately laminated so that the insulating layer 211a1 is interposed between the conductive layers 212a1 and 212a2, the insulating layer 211a2 is interposed between the conductive layers 212a2 and 212a3, and the insulating layer 211a3 is interposed between the conductive layers 212a3 and 212a4, providing the measurement substrate 10C.

Figure 11:
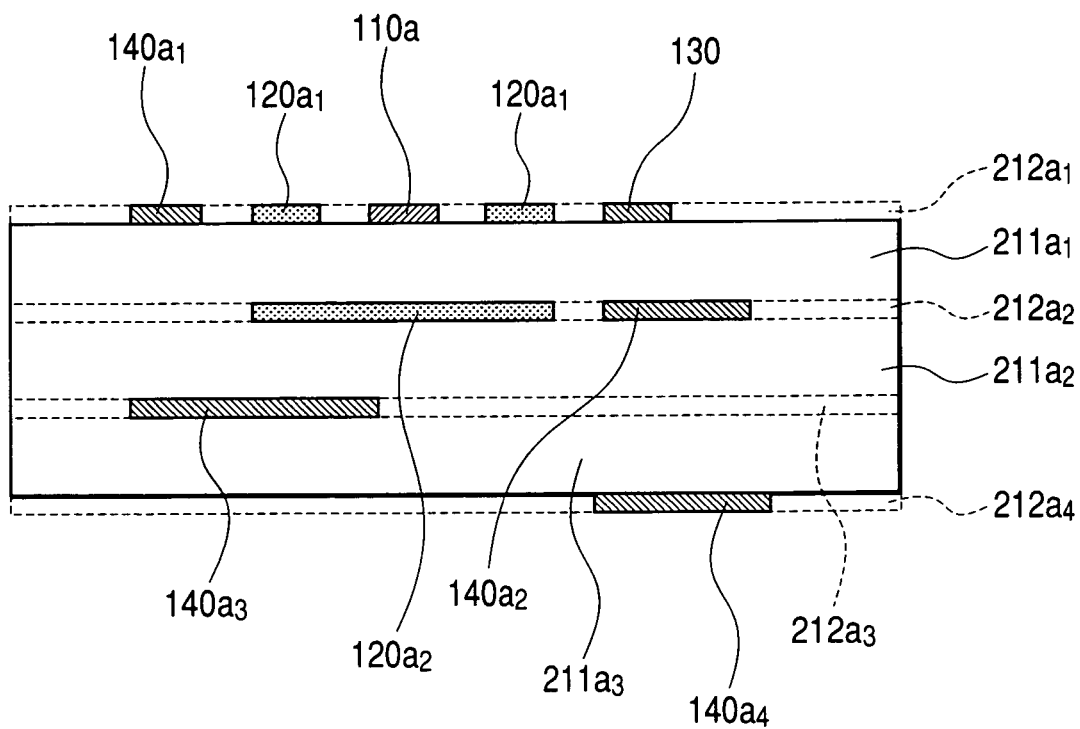
FIG. 11 is a schematic cross sectional view illustrating a schematic structure of the measurement substrate according to the second embodiment.
Figure 12:
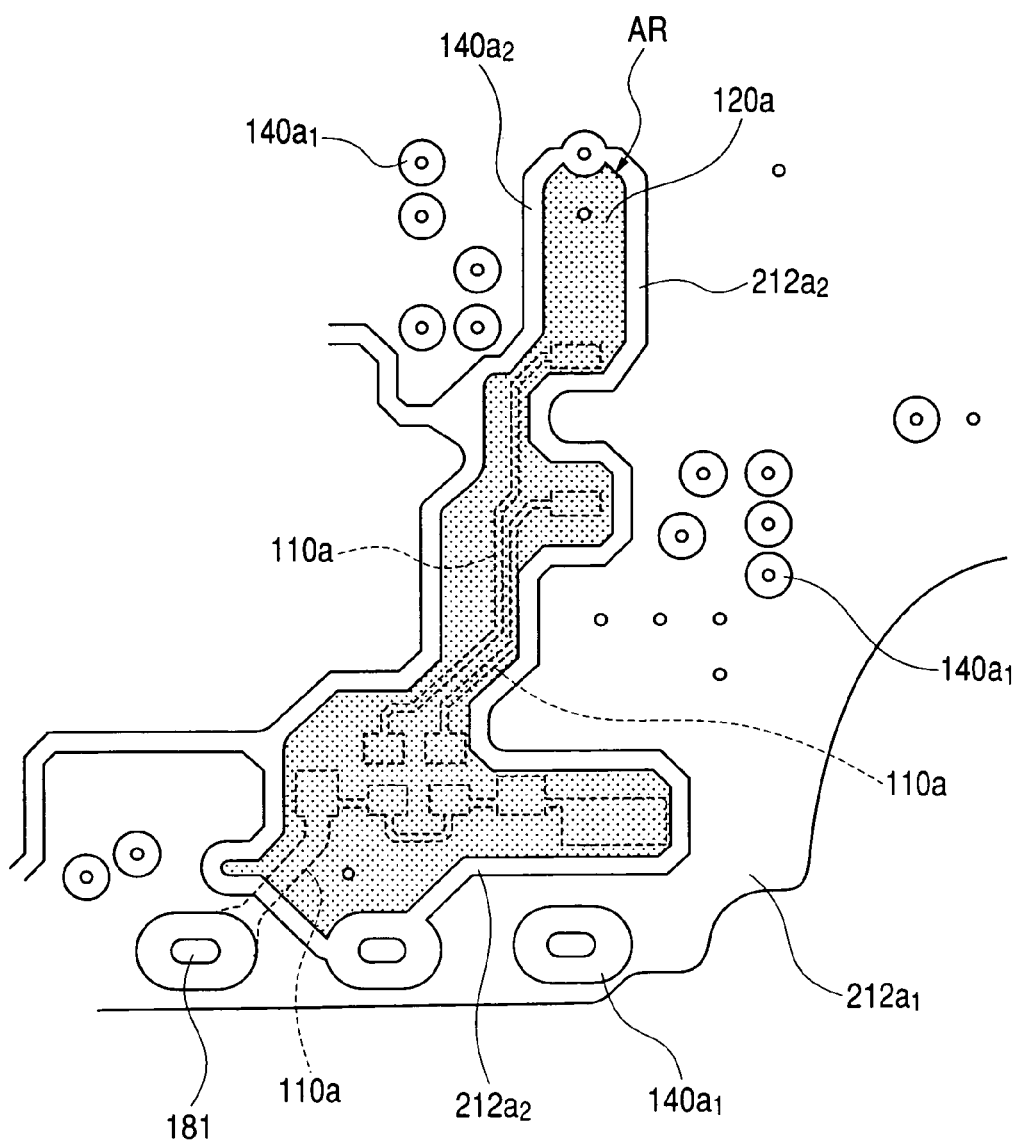
FIG. 12 is a view showing conductive patterns arranged in the measurement substrate shown in FIG. 11 according to the second embodiment.

As shown in FIGS. 11 and 12, the signal input patterns 110a corresponding to signal input patterns 110 of the first embodiment are formed in the conductive layer 212a1 which is one surface portion of the measurement substrate 10C. The conductive layer 212a1 is referred as "surface conductive layer 212a1".

The different potential patterns 140a1 corresponding to the different potential patterns 140 are formed in the conductive layer 212a1, and the guard pattern 120a1 corresponding to the guard pattern 120 of the first embodiment is mounted in the surface conductive layer 212a1, which are the same manner as the first embodiment, respectively.

As shown in FIG. 11, the different potential patterns 140a2, 140a3, and 140a4 are also formed in the conductive layers 212a2, 212a3, and 212a4, respectively.

In addition, as shown in FIGS. 11 and 12, the guard pattern 120a2 is formed in the conductive layer 212a2 that is adjacent to the surface conductive layer 212a1 so as to be arranged in at least a portion of an area AR of the conductive layer 212a2, area which is opposite to the signal input patterns 110a of the surface conductive layer 212a1. The conductive layer 212a2 is also referred as "intermediate conductive layer 212a2".

According to the measurement substrate 10 of this second embodiment, the guard pattern 120a2 effectively prevents the leakage current from occurring between the signal input patterns 110a and the different potential patterns 140a2 to 140a4 formed in the conductive layers 212a2 to 212a4 other than the surface conductive layer 212a1, in addition to the effect that the guard pattern 120a1 prevents the leakage current from occurring between the signal input patterns 110a and the different potential patterns 140a1 formed in the surface conductive portion 212a1.

That is, as shown in FIG. 12, the guard pattern 120a2 formed in the intermediate conductive layer 212a2 can effectively shut off the paths through which the leakage current flows from the conductive layers 212a2 to 212a4 other than the surface conductive layer 212a1 to the signal input pattern 110a.

As described above, the measurement substrate 10C having the multilayered structure can make improve the packaging density of the measurement substrate 10C and compact the size thereof while keeping the effect of preventing the affects of the leakage current with respect to the signal input patterns 110.

In addition, in each of the embodiments and modifications, the constant potential of the conductive pattern 109c is substantially set within a range from 80 percent or more to 120 percent or less of the potential of each of the signal input patterns 110 so that the potential difference between each signal input pattern 110 and the guard pattern 120 is set to no less than 0.5 V.

Assuming that the potential of the guard pattern 120 is set to less than 80 percent of each potential of each signal input pattern 110 or to more than 120 percent thereof, the potential difference between each signal input pattern 110 and the guard pattern 120 increases so that the leakage current increases based on Ohm's law, whereby the leakage current may affect the measurement accuracy of the gas concentration of the gas concentration measuring apparatus 1.

It is preferable to set, therefore, the potential of the guard pattern 120 within a range from 80 percent or more to 120 percent or less of the potential of each of the signal input patterns 110.

Similarly, assuming that the potential difference between each signal input pattern 110 and the guard pattern 120 is no less than 0.5 V, the leakage current increases based on Ohm's law so that the leakage current may affect the measurement accuracy of the gas concentration of the gas concentration measuring apparatus 1.

It is preferable to set, therefore, the potential difference between the guard pattern 120 and each of the signal input patterns 110 of approximately less than 0.5 V.

More preferably, the potential difference between the guard pattern 120 and each of the signal input patterns 110 may be set to approximately less than 0.2 V.

When setting the potential difference between the guard pattern 120 and each of the signal input patterns 110 may be set to approximately less than 0.2 V, it may be possible to more prevent the leakage current flowing between the guard pattern 120 and each of the signal input patterns 110, thereby more improving the measurement accuracy of the sensor current.

Moreover, in each of the embodiments and modifications, it is desirable to set the input impedance of the connection terminal 181 of approximately 1 mega ohms (MΩ) or more.

In a case of setting the input impedance of the connection terminal 181 to approximately 1 MΩ or more, the sensor current decreases so that it is particularly effective to prevent the leakage current from occurring between the signal input patterns 110 and the different potential patterns 140.

Furthermore, in each of the embodiments and modifications, it is preferable to set the direct current impedance of each of the signal input patterns 110 with respect to the connection terminal 181 to approximately 2 kΩ or less.

When setting the direct current impedance of each of the signal input patterns 110 with respect to the connection terminal 181 to approximately 2 kΩ or less, the sensor current decreases so that it is especially effective to prevent the leakage current from occurring between the signal input patterns 110 and the different potential patterns 140.

Still furthermore, in each of the embodiments and modifications, it is acceptable to set the potential differences between the different potential patterns 140 and the signal input patterns 110 to 4 V or more, respectively.

When setting the potential differences between the different potential patterns 140 and the signal input patterns 110 to 4 V or more, respectively, the sensor current decreases so that it is particularly excellent to prevent the leakage current from occurring between the signal input patterns 110 and the different potential patterns 140.

Moreover, in each of the embodiments and modifications, the signal processing circuit 100 comprises three operational amplifiers and the resistor, but the present invention is not limited to the structure.

That is, any signal processing circuit having various circuit structures may be used as the signal processing circuit 100 so long as it has the function of measuring the sensor current according to the sensor current outputted from the gas sensor.

Still furthermore, in each of the embodiments and modifications, the gas sensor measures the concentration of the NOx, but the gas sensor may measure CO, HC, or other similar materials.

While there has been described what is at present considered to be the embodiment and modifications of the invention, it will be understood that various modifications which are not described yet may be made therein, and it is intended to cover in the appended claims all such modifications as fall within the true spirit and scope of the invention.

This application is based upon and claims the benefit of priority of the prior Japanese Patent Application 2002-377918 filed on Dec. 26, 2002, and the prior Japanese Patent Application 2003-369493 filed on Oct. 29, 2003 so that the contents of which are incorporated herein by reference.

What is claimed is:

1. A gas concentration measuring apparatus comprising:

a gas sensor configured to measure a concentration of a specified gas component contained in a gas and to output a sensor current corresponding to the measured concentration of the specified gas component; and a measurement substrate where an electric circuit is formed, said electric circuit being electrically connected to the gas sensor and including a signal processing circuit configured to measure the sensor current outputted from the gas sensor, wherein said electric circuit comprises:

a connection terminal electrically connected to the gas sensor and configured to receive the sensor current from the gas sensor, said connection terminal having input impedance of 500 kΩ or over;

a conductive pattern portion having conductivity and formed in the measurement substrate; and an electric component mounted on the conductive pattern portion, said conductive pattern portion including:

a signal input pattern electrically connected to the connection terminal, said signal input pattern having direct current impedance with respect to the connection terminal, said direct current impedance being 10 percent or less of the input impedance of the connection terminal;

a different potential pattern having a potential difference of 2 V or over from a potential of the signal input pattern; and a guard pattern having a substantially constant potential and a potential difference of less than 0.5 V from the potential of the signal input pattern, said guard pattern being arranged on at least a portion of the measurement substrate, said at least portion of the measurement substrate being located between the signal input pattern and the different potential pattern, wherein the conductive pattern portion includes a signal measurement pattern constituting the signal processing circuit, a potential of the signal measurement pattern depends on that of the signal input pattern, the signal processing circuit comprises an operational amplifier, the signal input pattern is connected to a non-reverse input terminal of the operational amplifier so that the potential of the signal input pattern is input to the operational amplifier via the non-reverse input terminal thereof, an output terminal of the operational amplifier is connected to a reverse input terminal thereof so that the operational amplifier is configured to output, via the output terminal, a voltage that substantially equals to the potential of the signal input pattern, and the guard pattern is electrically connected to the signal measurement pattern.

2. The gas concentration measuring apparatus according to claim 1, wherein said guard pattern has a potential difference of less than 0.2 V from the potential of the signal input pattern.

3. The gas concentration measuring apparatus according to claim 1, wherein said input impedance of the connection terminal has 1 MΩ or more.

4. The gas concentration measurement apparatus according to claim 1, wherein said signal input pattern has direct current impedance of 2 kΩ or less from the input impedance of the connection terminal.

5. The gas concentration measurement apparatus according to claim 1, wherein said different potential pattern has a potential difference from the potential of the signal input pattern, said potential difference being 4 V or more.

6. The gas concentration measurement apparatus according to claim 1, wherein said signal input pattern includes a plurality of signal input patterns, said different potential pattern includes a plurality of different potential patterns, and said measurement substrate comprises a surface conductive layer where the signal input patterns, the different potential patterns, and the guard pattern are formed; and an insulating layer on which the surface conductive layer is mounted, and wherein said at least portion of the measurement substrate is located at a distance between at least one of the signal input patterns and at least one of the different potential patterns, said at least one of the signal input patterns and at least one of the different potential patterns being adjacent to each other.

7. The gas concentration measurement apparatus according to claim 1, wherein said signal input pattern includes a plurality of signal input patterns, said different potential pattern includes a plurality of different potential patterns, said guard pattern includes a plurality of guard patterns, said measurement substrate comprises a plurality of conductive layers; and a plurality of insulating layers so that the conductive layers and the insulating layers are alternately laminated with each other, one of said conductive layers corresponding to a surface portion of the measurement substrate, another one of said conductive layers being adjacent to the one of the conductive layers through one of the insulating layers interposed therebetween, said signal input patterns are formed in the one of the conductive layers, said different potential patterns are formed in the one of the conductive layers, said guard patterns are formed in both of the one of the conductive layers and another one thereof, respectively, said at least portion of the measurement substrate is located at a distance between at least one of the signal input patterns and at least one of the different potential patterns in the one of the conductive layers, said at least one of the signal input patterns and at least one of the different potential patterns is adjacent to each other therein, and wherein at least one of said guard patterns formed in another one of said conductive layers is arranged in an area of another one of the conductive layers, said area being opposite to at least one of the signal input patterns formed in the one of the conductive layers.

8. The gas concentration measurement apparatus according to claim 1, wherein said signal processing circuit comprises an operational amplifier having non-reverse input terminal, a reverse input terminal and an output terminal, said reverse input terminal being electrically connected to the connection terminal, said operational amplifier being configured to control that the potential applied on the non-reverse input terminal substantially coincides with the potential of the connection terminal, said non-reverse input terminal of the operational amplifier being electrically connected to a portion of the signal measurement pattern, and said guard pattern is electrically connected to the portion of the signal measurement pattern.

9. The gas concentration measurement apparatus according to claim 1, wherein said guard pattern is arranged to surround the signal input pattern.

10. The gas concentration measurement apparatus according to claim 1, wherein said different potential pattern comprises an exposed portion around which no insulating coating is formed, and a coating portion around which an insulating coating is formed, and said guard pattern comprises an exposed adjacent portion arranged adjacent to the exposed coating portion, and a coating adjacent portion arranged adjacent to the coating portion, said exposed adjacent portion being formed with no insulating film therearound, said coating adjacent portion being formed with an insulating film therearound.

11. The gas concentration measurement apparatus according to claim 1, wherein said gas sensor comprises a pair of sensor cells each of which outputs the sensor current, said measurement substrate comprises a pair of the signal processing circuits, one of said signal processing circuit is electrically connected to one of said sensor cells, other of said signal processing circuits is electrically connected to other of said sensor cells, one of said signal processing circuits is configured to correct the sensor current outputted from one of said sensor cells according to the sensor current measured and outputted from the other of the signal processing circuit.

12. The gas concentration measurement apparatus according to claim 1, wherein said specified gas component is one of NOx, CO and HC.

13. A gas concentration measuring apparatus comprising:
a gas sensor configured to measure a concentration of a specified gas component contained in a gas and to output a sensor current corresponding to the measured concentration of the specified gas component; and
a measurement substrate where an electric circuit is formed, said electric circuit being electrically connected to the gas sensor and including a signal processing circuit configured to measure the sensor current outputted from the gas sensor, wherein said electric circuit comprises:
a connection terminal electrically connected to the gas sensor and configured to receive the sensor current from the gas sensor, said connection terminal having input impedance of 500 k$\Omega$ or over;
a conductive pattern portion having conductivity and formed in the measurement substrate; and
an electric component mounted on the conductive pattern portion, said conductive pattern portion including:
a signal input pattern electrically connected to the connection terminal, said signal input pattern having direct current impedance with respect to the connection terminal, said direct current impedance being 10 percent or less of the input impedance of the connection terminal;
a different potential pattern having a potential difference of 2 V or over from a potential of the signal input pattern; and
a guard pattern having a substantially constant potential within a range from 80 percent or more to 120 percent or less of the potential of the signal input pattern, said guard pattern being arranged on at least a portion of the measurement substrate, said at least portion of the measurement substrate being located between the signal input pattern and the different potential pattern, wherein the conductive pattern portion includes a signal measurement pattern constituting the signal processing circuit, a potential of the signal measurement pattern depends on that of the signal input pattern, the signal processing circuit comprises an operational amplifier, the signal input pattern is connected to a non-reverse input terminal of the operational amplifier so that the potential of the signal input pattern is input to the operational amplifier via the non-reverse input terminal thereof, an output terminal of the operational amplifier is connected to a reverse input terminal thereof so that the operational amplifier is configured to output, via the output terminal, a voltage that substantially equals to the potential of the signal input pattern, and the guard pattern is electrically connected to the signal measurement pattern.

14. The gas concentration measuring apparatus according to claim 13, wherein said guard pattern has a potential difference of less than 0.2 V from the potential of the signal input pattern.

15. The gas concentration measuring apparatus according to claim 13, wherein said input impedance of the connection terminal has 1 M Ω or more.

16. The gas concentration measurement apparatus according to claim 13, wherein said signal input pattern has direct current impedance of 2 kΩ or less from the input impedance of the connection terminal.

17. The gas concentration measurement apparatus according to claim 13, wherein said different potential pattern has a potential difference from the potential of the signal input pattern, said potential difference being 4 V or more.

18. The gas concentration measurement apparatus according to claim 13, wherein said signal input pattern includes a plurality of signal input patterns, said different potential pattern includes a plurality of different potential patterns, and said measurement substrate comprises a surface conductive layer where the signal input patterns, the different potential patterns, and the guard pattern are formed; and an insulating layer on which the surface conductive layer is mounted, and
wherein said at least portion of the measurement substrate is located at a distance between at least one of the signal input patterns and at least one of the different potential patterns, said at least one of the signal input patterns and at least one of the different potential patterns being adjacent to each other.

19. The gas concentration measurement apparatus according to claim 13, wherein said signal input pattern includes a plurality of signal input patterns, said different potential pattern includes a plurality of different potential patterns, said guard pattern includes a plurality of guard patterns, said measurement substrate comprises a plurality of conductive layers; and a plurality of insulating layers so that the conductive layers and the insulating layers are alternately laminated with each other, one of said conductive layers corresponding to a surface portion of the measurement substrate, another one of said conductive layers being adjacent to the one of the conductive layers through one of the insulating layers interposed therebetween, said signal input patterns are formed in the one of the conductive layers, said different potential patterns are formed in the one of the conductive layers, said guard patterns are formed in both of the one of the conductive layers and another one thereof, respectively, said at least portion of the measurement substrate is located at a distance between at least one of the signal input patterns and at least one of the different potential patterns in the one of the conductive layers, said at least one of the signal input patterns and at least one of the different potential patterns is adjacent to each other therein, and
wherein at least one of said guard patterns formed in another one of said conductive layers is arranged in an area of another one of the conductive layers, said area being opposite to at least one of the signal input patterns formed in the one of the conductive layers.

20. The gas concentration measurement apparatus according to claim 13, wherein said signal processing circuit comprises an operational amplifier having non-reverse input terminal, a reverse input terminal and an output terminal, said reverse input terminal being electrically connected to the connection terminal, said operational amplifier being configured to control that the potential applied on the non-reverse input terminal substantially coincides with the potential of the connection terminal, said non-reverse input terminal of the operational amplifier being electrically connected to a portion of the signal measurement pattern, and said guard pattern is electrically connected to the portion of the signal measurement pattern.

21. The gas concentration measurement apparatus according to claim 13, wherein said guard pattern is arranged to surround the signal input pattern.

22. The gas concentration measurement apparatus according to claim 13, wherein said different potential pattern comprises an exposed portion around which no insulating coating is formed, and a coating portion around which an insulating coating is formed, and said guard pattern comprises an exposed adjacent portion arranged adjacent to the exposed coating portion, and a coating adjacent portion arranged adjacent to the coating portion, said exposed adjacent portion being formed with no insulating film therearound, said coating adjacent portion being formed with an insulating film therearound.

23. The gas concentration measurement apparatus according to claim 13, wherein said gas sensor comprises a pair of sensor cells each of which outputs the sensor current, said measurement substrate comprises a pair of the signal processing circuits, one of said signal processing circuit is electrically connected to one of said sensor cells, other of said signal processing circuits is electrically connected to other of said sensor cells, one of said signal processing circuits is configured to correct the sensor current outputted from one of said sensor cells according to the sensor current measured and outputted from the other of the signal processing circuit.

24. The gas concentration measurement apparatus according to claim 13, wherein said specified gas component is one of nitrogen oxides, carbon monoxide, and hydrocarbon.

* * * * *